US00PP14688P29

(12) United States Plant Patent
Hipkin

(10) Patent No.: US PP14,688 P2
(45) Date of Patent: Apr. 13, 2004

(54) HEBE PLANT NAMED 'SUNSTREAK'

(50) Latin Name: *Hebe hybrida*
Varietal Denomination: Sunstreak

(76) Inventor: Paul Hipkin, 6 Hodgson Road, Pakowai R.D.3, Napier (NZ)

( * ) Notice: Subject to any disclaimer, the term of this patent is extended or adjusted under 35 U.S.C. 154(b) by 0 days.

(21) Appl. No.: 10/452,069

(22) Filed: Jun. 2, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A distinct cultivar of Hebe plant named 'Sunstreak', characterized by its upright and somewhat outwardly spreading plant form; freely branching habit; dense and bushy growth habit; and grayed green and pale yellow variegated foliage.

1 Drawing Sheet

Botanical classification/cultivar designation: *Hebe hybrida* cultivar Sunstreak.

BACKGROUND OF THE INVENTION

The present Invention relates to a new and distinct cultivar of Hebe plant, botanically known as *Hebe hybrida*, and hereinafter referred to by the name 'Sunstreak'.

The new Hebe was discovered by the Inventor in 1999 in a controlled environment in Pirimai, Napier, New Zealand, as a naturally-occurring whole plant mutation of the *Hebe hybrida* cultivar Wiri Image, not patented. The new Hebe was selected by the Inventor on the basis of its variegated foliage as plants of the cultivar Wiri Image did not have variegated foliage.

Asexual reproduction of the new Hebe by cuttings in a controlled environment in Oak Road, New Zealand since 2000, has shown that the unique features of this new Hebe are stable and reproduced true to type in successive generations.

SUMMARY OF THE INVENTION

Plants of the cultivar Sunstreak have not been observed under all possible environmental conditions. The phenotype may vary somewhat with variations in environment such as temperature and light intensity without, however, any variance in genotype.

The following traits have been repeatedly observed and are determined to be the unique characteristics of 'Sunstreak'. These characteristics in combination distinguish 'Sunstreak' as a new and distinct cultivar:

1. Upright and somewhat outwardly spreading plant form.
2. Freely branching, dense and bushy growth habit.
3. Grayed green and pale yellow variegated foliage.

Plants of the cultivar Sunstreak can be compared to plants of the Hebe cultivar Waireka. In side-by-side comparisons conducted in Oak Road, New Zealand, plants of the new Hebe differed from plants of the cultivar Waireka in the following characteristics:

1. Plants of the new Hebe were more upright than plants of the cultivar Waireka.
2. Plants of the new Hebe had narrower leaves than plants of the cultivar Waireka.

3. Plants of the new Hebe and the cultivar Waireka differed in leaf variegation pattern.

BRIEF DESCRIPTION OF THE PHOTOGRAPHS

The accompanying colored photographs illustrate the overall appearance of the new Hebe, showing the colors as true as it is reasonably possible to obtain in colored reproductions of this type. Colors in the photographs may differ slightly from the color values cited in the detailed botanical description which accurately describe the colors of the new Hebe.

The photograph at the top of the sheet comprises a side perspective view of a typical plant of 'Sunstreak' grown in a container.

The photographs at the bottom of the sheet are close-up views of typical leaves of 'Sunstreak'.

DETAILED BOTANICAL DESCRIPTION

In the following description, color references are made to The Royal Horticultural Society Colour Chart, 2001 Edition, except where general terms of ordinary dictionary significance are used. Plants used for the photographs and the following description were about 13 months old and grown under outdoor field conditions which closely approximate commercial production conditions in Boskoop, The Netherlands. During the production of the plants, day temperatures ranged from 6 to 15° C. and night temperatures ranged from 2 to 8° C.

Botanical classification: *Hebe hybrida* cultivar Sunstreak.
Parentage: Naturally-occurring whole plant mutation of the *Hebe hybrida* cultivar Wiri Image, not patented.
Propagation:
*Type.*—By softwood cuttings.
*Time to initiate roots.*—Summer: About 14 days at 25° C. Winter: About 21 days at 15° C.
*Time to produce a rooted cutting.*—Summer: About 60 days at 21° C. Winter: About 80 days at 15° C.
*Root description.*—Fine and freely branching.
Plant description:
*Form.*—Evergreen shrub; upright and outwardly spreading; inverted triangle, flattened globular plant form; freely branching, dense and bushy habit; moderately vigorous.

*Plant height.*—About 39 cm.

*Plant diameter.*—About 37 cm.

*Lateral branches.*—Quantity per plant: About 15; pinching is not required, but will improve branching. Length: About 22.2 cm. Diameter: About 5 to 6 mm. Internode length: About 8 mm. Strength: Strong. Texture: Moderately pubescent. Color: N200B to 138B.

*Foliage description.*—Arrangement: Opposite, simple; sessile. Length: About 6 cm. Width: About 1.7 cm. Shape: Elliptic to narrowly elliptic. Apex: Acute. Base: Cuneate. Margin: Entire. Texture, upper and lower surfaces: Slightly leathery; smooth, glabrous. Venation pattern: Pinnate. Color: Developing foliage, upper surface: Center, 137A; random longitudinal streaks, 138B to 191B; irregular margins, 150D to 4D to 8D. Developing foliage, lower surface: N138C; irregular margins, 8D. Fully expanded foliage, upper surface: Center, 189A; random longitudinal streaks, 191A to 191B; irregular margins, 8D to 9D. Fully expanded foliage, lower surface: Slightly more green than 189B; irregular margins, 9D. Venation, upper surface: Midvein, 189A to 191A to 191B; lateral veins not visible. Venation, lower surface: Midvein, 138A; lateral veins not visible.

Flower description: Flower development has not been observed.

Disease/pest resistance: Plants of the new Hebe have not been noted to be resistant to pathogens and pests common to Hebe.

Temperature tolerance: Plants of the new Hebe are hardy to U.S.D.A. Zone 8 and have been observed to tolerate temperatures as high as 35° C.

It is claimed:

1. A new and distinct cultivar of Hebe plant named 'Sunstreak', as illustrated and described.

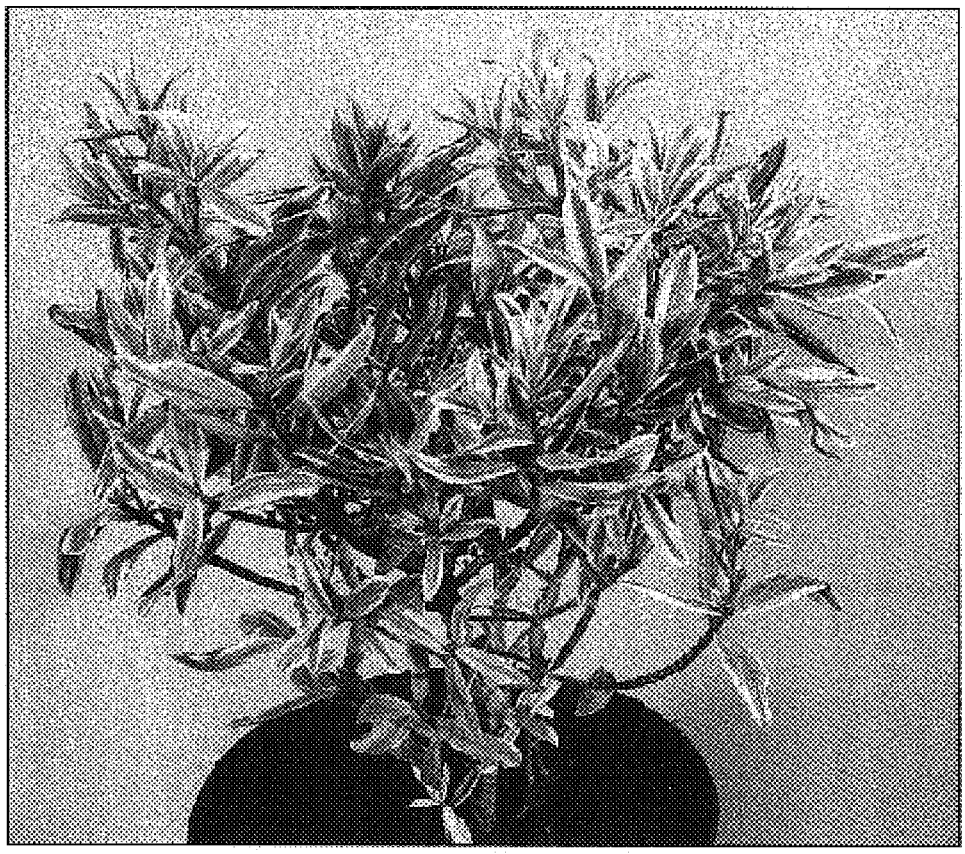
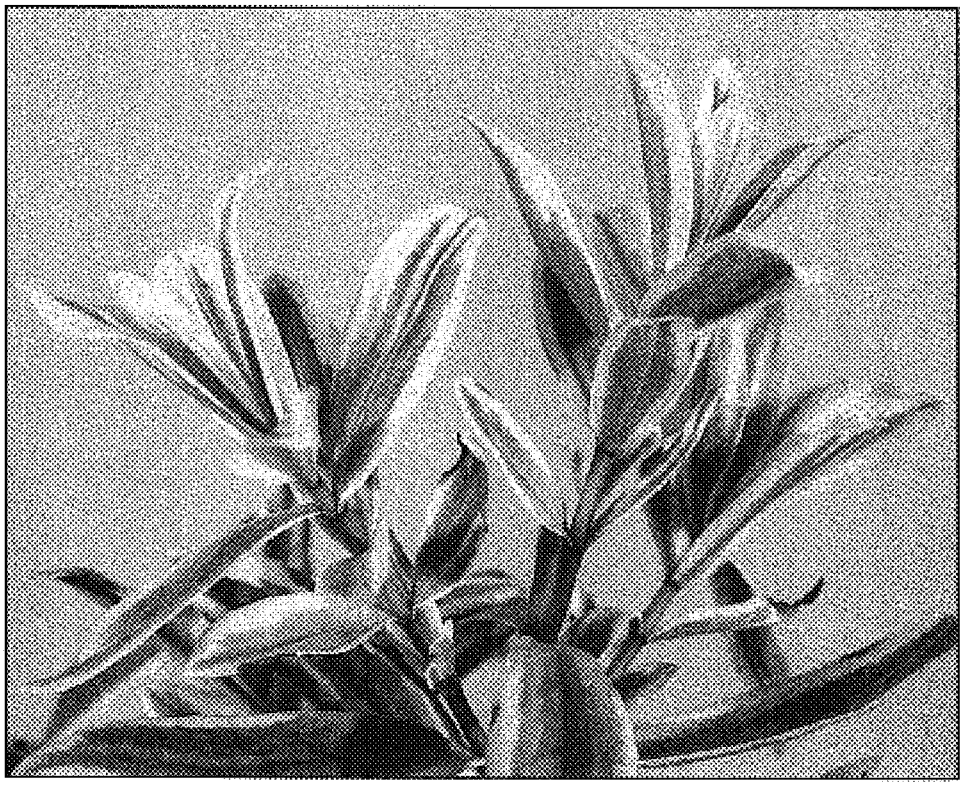

* * * * *